(12) United States Patent
Grüner et al.

(10) Patent No.: US 11,992,236 B2
(45) Date of Patent: *May 28, 2024

(54) MEDICAL INSTRUMENT

(71) Applicant: KARL STORZ SE & Co. KG, Tuttlingen (DE)

(72) Inventors: Sven Grüner, Tuttlingen (DE); Robin Merz, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/182,484

(22) Filed: Mar. 13, 2023

(65) Prior Publication Data

US 2023/0210547 A1 Jul. 6, 2023

Related U.S. Application Data

(63) Continuation of application No. 16/935,685, filed on Jul. 22, 2020, now Pat. No. 11,660,107.

(30) Foreign Application Priority Data

Aug. 5, 2019 (DE) ...................... 10 2019 121 099.2

(51) Int. Cl.
*A61B 17/29* (2006.01)
*A61B 17/00* (2006.01)

(52) U.S. Cl.
CPC .... *A61B 17/29* (2013.01); *A61B 2017/00323* (2013.01); *A61B 2017/2902* (2013.01); *A61B 2017/2927* (2013.01)

(58) Field of Classification Search
CPC .............. A61B 17/29; A61B 2017/003; A61B 2017/2901; A61B 2017/2905; A61B 2090/508; A61B 90/50
See application file for complete search history.

(56) References Cited

U.S. PATENT DOCUMENTS

| | | |
|---|---|---|
| 2010/0041945 A1 | 2/2010 | Isbell, Jr. |
| 2010/0042077 A1 | 2/2010 | Okada |
| 2013/0218141 A1 | 8/2013 | Hinman et al. |

FOREIGN PATENT DOCUMENTS

| | | |
|---|---|---|
| DE | 19509115 A1 | 9/1996 |
| DE | 102007038386 A1 | 3/2008 |

(Continued)

*Primary Examiner* — Brooke Labranche
(74) *Attorney, Agent, or Firm* — Eversheds Sutherland (US) LLP

(57) ABSTRACT

This application is directed to a medical instrument with a hollow shaft, an actuating unit at the proximal end and an instrument tip with an instrument at the distal end, the instrument actuated via an actuating element, the element being in connection with the actuating unit and the instrument tip being pivotable relative to the shaft via a joint mechanism; the joint mechanism having pivoting members with proximal-side drive via steering wires such that movement of the proximal-side drive causes movement of the distal-side pivoting members and pivoting of the instrument tip; and a trigger mechanism with which the steering wires can be brought into a relaxed state that releases the articulation of the instrument tip. In order for the medical instrument to be cleaned and ensure that the medical instrument is safely removed even if the proximal-side drive fails, the trigger mechanism is a purely mechanical trigger mechanism.

3 Claims, 3 Drawing Sheets

(56) References Cited

FOREIGN PATENT DOCUMENTS

| | | | |
|---|---|---|---|
| EP | 2486876 | A1 | 8/2012 |
| WO | 03/105563 | A2 | 12/2003 |
| WO | 2014133180 | A1 | 9/2014 |

MEDICAL INSTRUMENT

TECHNICAL FIELD

The invention relates to a medical instrument with a hollow shaft, an actuating unit arranged at the proximal end of the shaft and an instrument tip with an instrument arranged at the distal end, wherein the instrument can be actuated via an actuating element mounted axially displaceably in the shaft, said element being in an operative connection with the actuating element on the proximal side and the instrument tip being pivotable relative to the longitudinal axis of the shaft via a joint mechanism, the joint mechanism consisting of pivoting members arranged at the distal end of the shaft, which are connected with a proximal-side drive via steering wires running in the longitudinal direction of the shaft in such a way that a movement of the proximal-side drive causes a corresponding relative movement of the distal-side pivoting members and thus a pivoting of the instrument tip as well as a trigger mechanism with which the steering wires can be brought into a relaxed state that releases the movability of the instrument tip independently from the actuation of the proximal-side drive.

BACKGROUND OF THE INVENTION

Pivoting members with three, four or more external steering wires/steering cables for bendable medical instruments are known in practice for hand-held and/or robotic instruments. For a sensitive control of the distal end of such a medical instrument, many thin steering wires/steering cables have proven to be more advantageous than a few thicker steering wires/steering cables since, among other things, a more even distribution of force can be achieved in all directions of deflection, and, moreover, thinner steering wires/steering cables allow for more space in the interior for electrical cables and the like.

A medical instrument with pivoting members controlled via steering wires/steering cables is known, for example, from US 2013/0218141 A1.

One disadvantage of these known instruments provided with steering wires/steering cables is that it is difficult to clean the many steering wires/steering cables that are arranged tightly in the shaft. In particular, when using steering cables, dirt can accumulate between the individual wires of the steering cables, which is difficult to remove.

In addition, the known instruments have the problem that if the proximal-side drive fails when the instrument tip is angled, it is no longer possible to move the instrument tip back into the undeflected position and remove the instrument from the operating area via the trocar. In the worst case, the surgeon must significantly increase the access in the patient in order to remove the trocar together with the angled instrument located therein.

A generic medical instrument is known from WO 2014/133180 A1. This known medical instrument comprises a trigger mechanism which is driven by a motor in order to be able to bring the steering wires into a relaxed state in the event of a failure of the pivot drive. In the event of a total failure of the energy supply, it is also not possible with this technical configuration to bring the steering wires into a relaxed state since, in this case, the motor drive of the trigger mechanism can no longer be actuated.

SUMMARY OF THE INVENTION

Based on this, the object of the invention is to design a medical instrument of the type mentioned at the outset in such a way that it is easy and effective to clean on the one hand and, moreover, ensures that the medical instrument can safely be removed even if the proximal-side drive fails.

The solution to this problem is characterized in that the trigger mechanism is designed as a purely mechanical trigger mechanism.

By using the purely mechanical trigger mechanism, it is possible at any time to transition the steering wires to a relaxed state regardless of the proximal-side drive, which makes it easier to clean the non-tensioned steering wires and also ensures that, when the steering wires are relaxed, the instrument tip can automatically be changed to the undeflected position when the medical device is removed from the trocar if the proximal-side drive were to fail or even a total power supply failure were to occur.

According to a practical embodiment of the invention, it is proposed that a shaft tube of the shaft can be displaced in the direction of the longitudinal axis of the shaft by means of the release mechanism in order to relax the steering wires. By displacing the shaft tube proximally, the steering wires are released at the distal end of the shaft so that the steering wires hang slackly without the leading action of the shaft tube, which allows the instrument tip to move freely regardless of the proximal-side drive. In this relaxed position of the steering wires, the steering wires and the interior of the hollow shaft tube can also be cleaned better and more thoroughly than if the steering wires were tensioned.

In a preferred first embodiment of the invention, it is proposed that the trigger mechanism be designed as a mechanical clamping mechanism. A mechanical clamping mechanism can be designed and operated in a structurally simple and low-maintenance manner.

Furthermore, it is proposed, according to the invention, that all steering wires can be relaxed simultaneously via the mechanical tensioning mechanism. The simultaneous relaxation of all steering wires of the medical instrument simplifies the use of the trigger mechanism and, in the event of a failure of the proximal-side drive, enables the medical instrument to be removed quickly and easily via the trocar, even if the instrument tip was previously bent.

According to a first embodiment of the design of the mechanical tensioning mechanism, it is proposed, according to the invention, that the mechanical tensioning mechanism consists of two levers, which are connected to one another in an articulated manner, with a first lever being pivotally mounted on the shaft tube with its free end and a second lever being pivotably mounted on the actuating unit with its free end. The design of the mechanical tensioning mechanism as a mechanism consisting of two pivotable levers represents a design which is easy to manufacture and also easy to operate.

According to a second practical embodiment of the design of the mechanical clamping mechanism, it is proposed according to the invention that the mechanical clamping mechanism is designed as a clamping thread with the shaft tube being displaceable in the direction of the longitudinal axis of the shaft by rotation about the longitudinal axis of the shaft. The clamping thread design is a simply constructed and easy-to-use variation of the mechanical clamping mechanism.

Finally, it is proposed in a second embodiment of the invention with respect to the design the trigger mechanism that the trigger mechanism consists of a separate drive for each steering wire.

BRIEF DESCRIPTION OF THE DRAWINGS

Further features and advantages of the invention are shown in the associated drawings in which an embodiment of a medical instrument, according to the invention, is only shown by way of example without limiting the invention to this embodiment. The drawings show the following.

DETAILED DESCRIPTION

Figure 1:
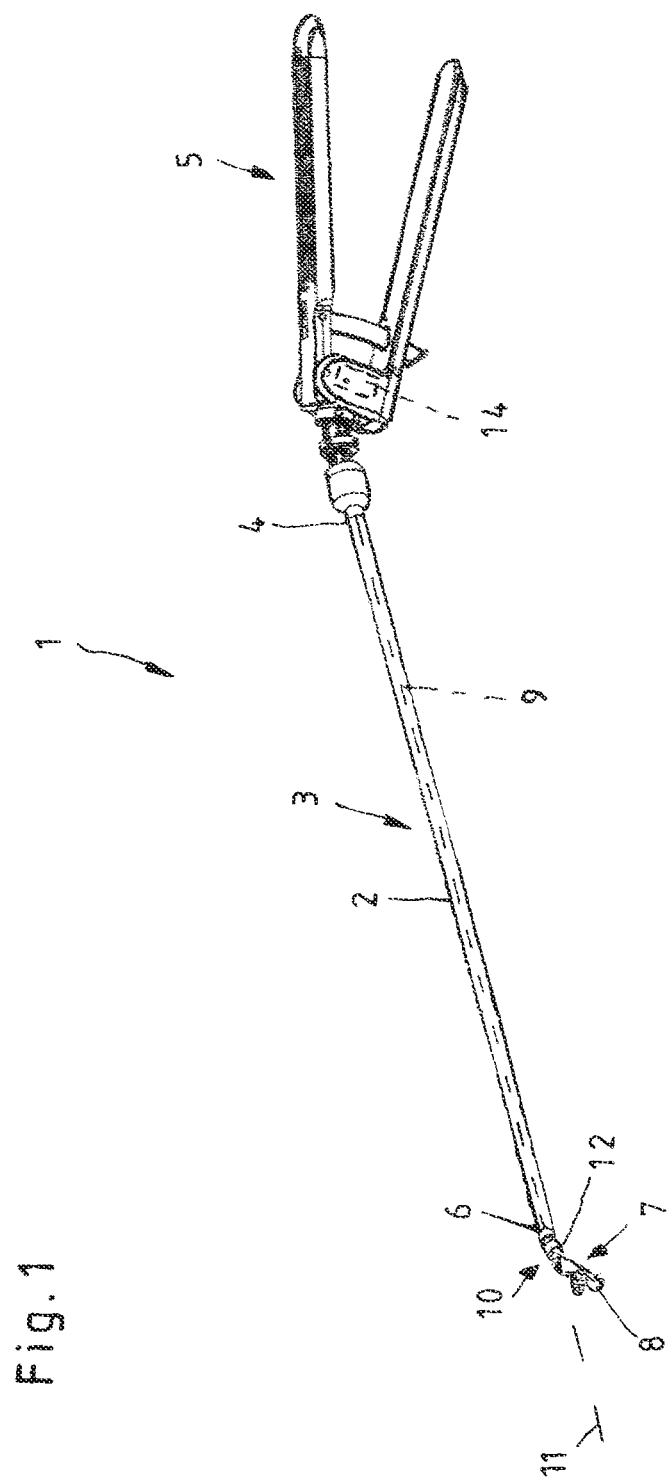
FIG. 1 shows a side perspective view of a medical instrument according to the prior art.

FIG. 1 shows a medical instrument 1 with a shaft 3 comprising a hollow shaft tube 2, an actuating unit 5 arranged at the proximal end 4 of the shaft 3 and an instrument tip 7 with an instrument 8 arranged at the distal end 6 of the shaft 3, the instrument 8 being able to be actuated via an actuating element 9 mounted axially displaceably in the shaft tube 2, with the shaft tube being in an operative connection with the actuating unit 5 on the proximal side.

The actuating unit 5 may be a manually operable handle or also a structural unit designed for robotic use, i.e., it may also be operable without any manual intervention.

The instrument 8 of the instrument tip 7 can be, for example, a tool provided with jaw parts, as shown in FIG. 1, or an endoscope, an applicator or the like.

The instrument tip 7 can be pivoted relative to the longitudinal axis 11 of the shaft 3 by means of a joint mechanism 10, the joint mechanism 10 consisting of pivoting members 12 arranged at the distal end 6 of the shaft 3 and having steering wires 13 running in the longitudinal direction of the shaft 3 (in particular FIG. 3) to a proximal-side drive 14 such that a movement of the proximal-side drive 14 causes a corresponding relative movement of the distal-side pivoting members 12 and thus a pivoting of the instrument tip 7.

Even if only the term steering wires 13 is used above and below, steering cables may also be used with respect to function, which is why the term steering wires 13 used is to be read and understood synonymously as a steering cable.

A disadvantage of the medical instruments 1 known from prior art and provided with steering wires 13 is that it is difficult to clean the many steering wires 13 arranged tightly in the shaft tube 2. In particular, when using steering wires 14 designed as steering cables, dirt can accumulate between the individual wires of the steering cables and is difficult to remove.

In addition, the known medical instruments 1 have the problem that if the proximal-side drive 14 fails when the instrument tip 7 is angled, it is no longer possible to move the instrument tip 7 back into the undeflected position and remove the medical instrument 1 from the operating area via a trocar. In the worst case, the surgeon must significantly increase the access in the patient in order to remove the trocar together with the angled medical instrument 1 located therein.

Figure 2:
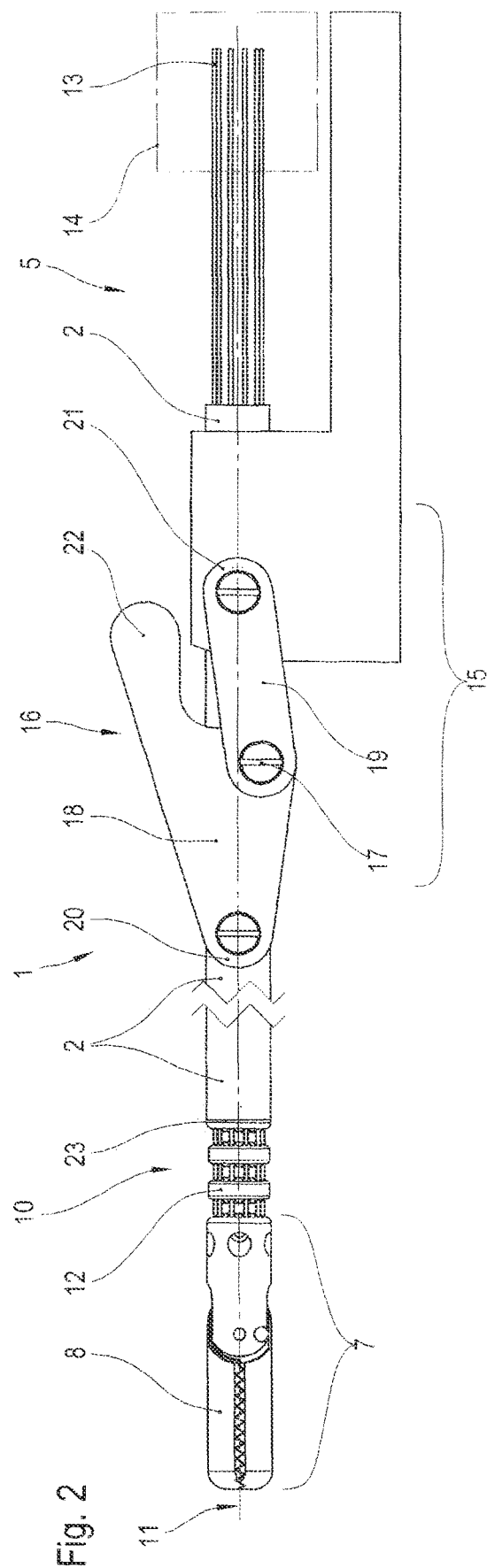
FIG. 2 shows an enlarged detail view of the distal shaft end and the proximal shaft end of a medical instrument according to the invention with the steering wires and the release mechanism in the tensioned position and FIG. 3 shows a view of FIG. 2 but with the steering wires and the trigger mechanism in the relaxed position.
Figure 3:
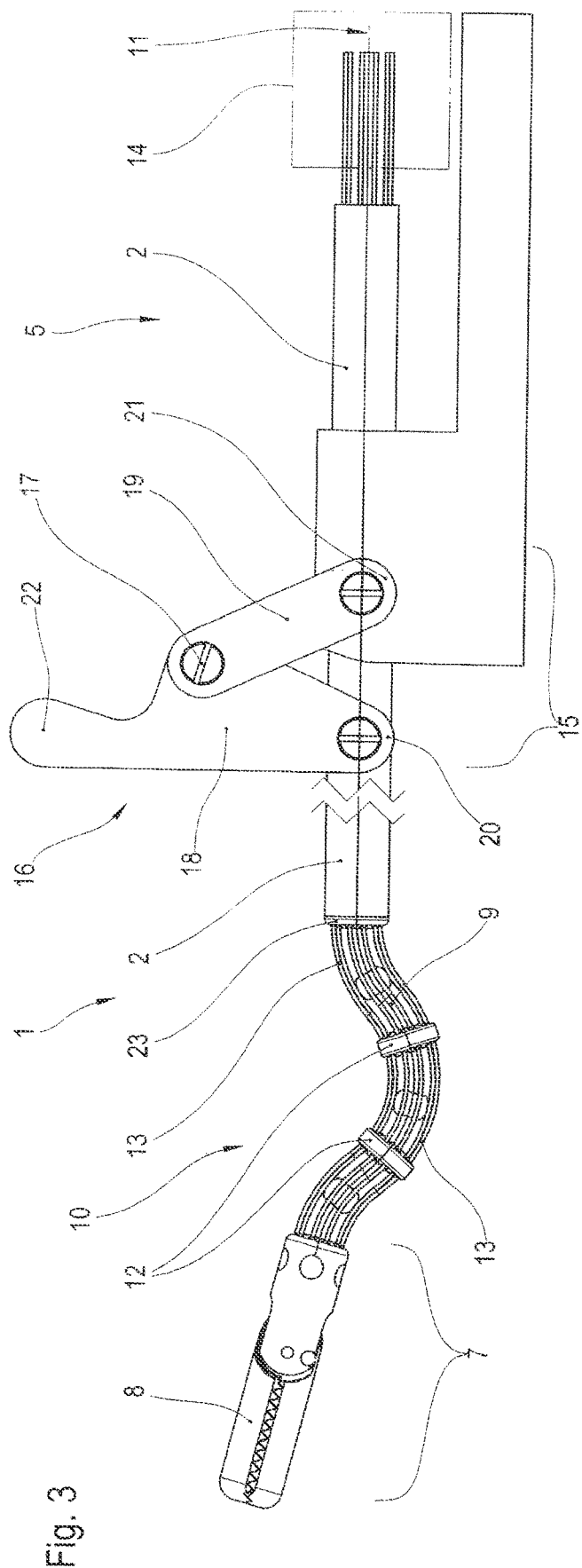

The medical instrument 1 shown in FIGS. 2 and 3 comprises a trigger mechanism 15 in the area of the actuating unit 5, by means of which the steering wires 13 can be transitioned to a relaxed state which releases the articulation of the instrument tip 7 independently of the actuation of the proximal-side drive 14.

In the embodiment shown, the trigger mechanism 15 is designed as a mechanical tensioning mechanism 16, by means of which all the steering wires 13 of the medical instrument 1 can be relaxed and tensioned again at the same time. This mechanical clamping mechanism 16 consists of two levers 18 and 19 which are articulated to one another via a common axis of rotation 17, a first lever 18 having its free end 20 pivotably mounted on the shaft tube 2 and the second lever 19 pivotably mounted with its free end 21 on the actuating unit 5. To actuate the mechanical clamping mechanism 16, a handle 22 is formed on the first lever 18.

The mode of operation of the trigger mechanism 15, which is designed as a mechanical clamping mechanism 16, is explained below with reference to FIGS. 2 and 3.

FIG. 2 shows the medical instrument 1 in the ready-to-use working position in which the steering wires 13 are arranged under tension inside the hollow shaft tube 2 of the shaft 3 and in which the instrument tip 7 can be angled by actuating the proximal-side drive 14 arranged in the actuating unit 5 via the steering wires 13 and the pivoting members 12 relative to the longitudinal axis 11 of the shaft 3.

In this tensioned position of the steering wires 13, the two levers 18 and 19 of the mechanical tensioning mechanism 16 are stretched one behind the other in the direction of the longitudinal axis 11 and aligned essentially parallel to the shaft tube 2.

In this position, the distal end 23 of the shaft tube 2 presses the pivoting members 12, which are freely displaceably mounted on the steering wires 13, distally towards the instrument tip 7. In this position, the instrument tip 7 can only be pivoted by means of the proximal-side drive 14.

If, starting from the tensioned position of the steering wires 13 shown in FIG. 2, the mechanical tensioning mechanism 16 is actuated and the two levers 18 and 19 are pivoted toward one another, as shown in FIG. 3, the mechanical tensioning mechanism 16 shown can be used displace the hollow shaft tube 2 of the shaft 3 proximally in order to relax the steering wires 13 in the direction of the longitudinal axis 11 of the shaft 3. The proximal displacement of the shaft tube 2 can be seen in FIG. 3 in the form of the proximal-side protrusion of the shaft tube 2 over the actuating unit 5.

By shifting the shaft tube 2 proximally, the steering wires 13 are released at the distal end 6 of the shaft 3 so that the steering wires hang slackly from the distal end 23 of the shaft tube 2 without the guiding action of the shaft tube 2, thereby allowing the instrument tip 7 to move freely regardless of the proximal-side drive 14 as may be necessary, for example, if the proximal-side drive 14 fails when the instrument tip 7 is angled.

In this relaxed position of the steering wires 13, the steering wires 13 and the interior of the hollow shaft tube 3 can also be cleaned better and more thoroughly than if the steering wires 13 were tensioned.

The displacement of the shaft tube 2 of the shaft 3 in the direction of the longitudinal axis 11 of the shaft 3 in order to relax the steering wires 13 can, alternatively to the embodiment shown as a tensioning thread 16 equipped with the two levers 18 and 19, also be achieved by tension thread with the shaft tube 2 being displaceable by a rotation about the longitudinal axis 11 of the shaft 3 in the direction of the longitudinal axis 11 of the shaft 3.

In order to achieve the displacement of the shaft tube 2 of the shaft 3 in the direction of the longitudinal axis 11 of the shaft 3 for relaxing the steering wires 13, further alternative embodiments are, for example, an eccentric tensioner or a latching mechanism or the like.

According to a second embodiment (not shown) of a design of the trigger mechanism 15, the trigger mechanism 15 may consist of a separate drive for each steering wire 13.

A medical instrument 1 designed as described above is characterized in that the use of the trigger mechanism 15 makes it possible to relax the steering wires 13 independently of the actuation of the proximal-side drive 14.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

LIST OF REFERENCE SIGNS

1 Medical instrument
2 Shaft tube
3 Shaft
4 Proximal end (shaft)
5 Actuating unit
6 Distal end (shaft)
7 Instrument tip
8 Instrument
9 Actuating element
10 Joint mechanism
11 Longitudinal axis
12 Pivoting member
13 Steering wire
14 Drive
15 Trigger mechanism
16 Clamping mechanism
17 Axis of rotation
18 Lever (first)
19 Lever (second)
20 Free end (first lever)
21 Free end (second lever)
22 Handle
23 Distal end (shaft tube)

We claim:

1. A medical instrument with a hollow shaft comprising a hollow shaft tube, an actuating unit arranged at the proximal end of the shaft and an instrument tip with an instrument arranged at the distal end of the shaft, wherein the instrument can be actuated via an actuating element mounted axially displaceably in the shaft, the actuating element being in an operative connection with the actuating unit on the proximal side and the instrument tip being pivotable relative to the longitudinal axis of the shaft via a joint mechanism;

the joint mechanism having pivoting members arranged on the distal end of the shaft are connected with a proximal-side drive via steering wires arranged inside the hollow shaft tube of the shaft and running in the longitudinal direction of the shaft in such a way that a movement of the proximal-side drive causes a corresponding relative movement of the distal-side pivoting members and thus a pivoting of the instrument tip as well as with a trigger mechanism with which the steering wires can be brought into a relaxed state that releases the articulation of the instrument tip, independently from the actuation of the proximal-side drive, characterized in that, the distal-side pivoting members and thus also the instrument tip stay in a fixed unmovable position between each movement of the proximal-side drive free of the use of a locking mechanism and in that, the trigger mechanism comprises a mechanical trigger mechanism enabling a free movement of the pivoting members in case of failure of the proximal side drive, wherein the hollow shaft tube of the shaft which coaxially surrounds the steering wires can be displaced in the direction of the longitudinal axis of the shaft for relaxing the steering wires through the use of the trigger mechanism;

characterized in that the trigger mechanism is designed as a mechanical clamping mechanism; and characterized in that the mechanical clamping mechanism comprises two articulated levers and, wherein a first lever is pivotably mounted with its free end on the hollow shaft tube, and a second lever is pivotably mounted with its free end on the actuating unit.

2. The medical instrument according to claim 1, characterized in that all the steering wires can be relaxed simultaneously through the use of the mechanical clamping mechanism.

3. The medical instrument according to claim 1, characterized in that the trigger mechanism comprises a separate drive for each steering wire.

* * * * *